(12) United States Patent
Quong

(10) Patent No.: US 6,375,968 B1
(45) Date of Patent: *Apr. 23, 2002

(54) ENCAPSULATED ACTIVE MATERIAL IMMOBILIZED IN HYDROGEL MICROBEADS

(75) Inventor: Douglas Quong, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/425,761

(22) Filed: Oct. 22, 1999

(51) Int. Cl.$^7$ ............................................. A01M 25/00
(52) U.S. Cl. ........................ 424/408; 424/84; 424/450; 424/488; 424/407
(58) Field of Search .......................... 424/408, 84, 450, 424/488, 486, 487, 407

(56) References Cited

U.S. PATENT DOCUMENTS

| | | |
|---|---|---|
| 3,577,515 A | 5/1971 | Vandegaer |
| 3,691,140 A | 9/1972 | Silver |
| 4,402,856 A | 9/1983 | Schnoring et al. |
| 4,487,759 A | 12/1984 | Nesbitt et al. |
| 4,532,123 A | 7/1985 | Gardner |
| 4,689,293 A | 8/1987 | Goosen et al. |
| 4,701,326 A | 10/1987 | Nelsen et al. |
| 4,708,861 A | 11/1987 | Popescu et al. |
| 4,746,513 A | 5/1988 | Smith |
| 4,755,377 A | 7/1988 | Steer |
| 4,911,928 A | 3/1990 | Wallach |
| 5,045,569 A | 9/1991 | Delgado |
| 5,089,606 A | 2/1992 | Cole et al. |
| 5,508,313 A | 4/1996 | Delgado et al. |
| 5,545,423 A * | 8/1996 | Soon-Schiong et al. |
| 5,645,844 A | 7/1997 | Henderson et al. |

FOREIGN PATENT DOCUMENTS

| | | |
|---|---|---|
| CA | 1044134 | 12/1978 |
| CA | 1179682 | 12/1984 |
| EP | 0 371 635 | 7/1996 |
| GB | 1236885 | 6/1971 |
| JP | S 58-183601 | 10/1983 |
| JP | S 59-139301 | 8/1984 |
| JP | 4310233 | 11/1992 |
| JP | 8-173794 | 7/1996 |
| WO | WO 87/01587 | 3/1987 |
| WO | WO 89/12450 | 12/1989 |
| WO | WO 94/12161 | 6/1994 |
| WO | WO 98/44912 | 10/1998 |
| WO | WO 98/54036 | 10/1998 |
| WO | WO 00/53159 | 9/2000 |

OTHER PUBLICATIONS

D. Quong, "DNA encapsulation within membrane coated alginate beads," Dept of Chemical Engineering, McGill University, Montreal, Canada, Jul. 1997.

* cited by examiner

*Primary Examiner*—Thurman K. Page
*Assistant Examiner*—Amy E Pulliam
(74) *Attorney, Agent, or Firm*—Arlene L. Hornilla; Dale A. Bjorkman (57) ABSTRACT

A microbead comprising a hydrophilic matrix having active-filled microcapsules entrained therein. Compositions comprising the microbeads suspended in solution are useful for delivering active material. The microbeads of the invention may be controllable by exposing the microbeads to high or low humidity or moisture.

27 Claims, 2 Drawing Sheets

ENCAPSULATED ACTIVE MATERIAL IMMOBILIZED IN HYDROGEL MICROBEADS

FIELD OF THE INVENTION

The invention relates broadly to a combination of encapsulation, immobilization and release of active material using hydrogel microbeads, where the active can be either water soluble or water insoluble. Specifically, the hydrogel microbeads immobilize encapsulated agricultural chemicals such as pheromones, herbicides, insecticides and pesticides, whereby the encapsulated active material is released into ambient air by diffusion through at least two paths sections: a microcapsule shell and a hydrophilic matrix.

BACKGROUND

Methods of eliminating unwanted pests from orchards, crops and forests frequently entail the use of organophosphate insecticides. Alternative methods involve insect mating disruption, where insect pheromones are used to control pests and protect agricultural crop. In insect mating disruption methods, the mating pheromone plume of a female insect is typically masked with other pheromone point sources. This reduces the likelihood of a male insect finding a female, and subsequently disrupts and reduces larvae production. The insect population of the next generation is thus decreased, as well as potential crop damage.

Conventional sprayable pheromone formulations are generally provided in liquid filled microcapsules containing an active. Typically, the microcapsules have a polyurea membrane that can be formed using an interfacial process involving an isocyanate and an amine. Microencapsulation by this method has been described for example in U.S. Pat. No. 4,487,759 (Nesbitt et al, 1984). These polyurea membranes allow actives to be released into the atmosphere for up to a total of 2–3 weeks for most insect pheromones. Membranes of polyurea capsules are generally semi-permeable, therefore active material can diffuse across the membranes and release slowly with time. Potentially, high concentrations of active in the air can be observed immediately upon delivery or spraying of encapsulated products. This may be attributable to a high occurrence of capsule bursts or potential leaks in microcapsules.

U.S. Pat. No. 4,532,123 teaches capsules containing a pharmaceutical active material in primary capsules, that are further encapsulated within a second membrane to create secondary capsules. The intracapsular liquid core of the secondary capsules contain enzymes which slowly hydrolyze the membrane of the primary capsules. This slow hydrolysis enables the slow release of active from the primary capsules into the larger capsular core for controlled delivery.

A Japanese paten, JP 8-173794 teaches encapsulation of an amine within small capsules of polymethyl methacrylate membranes. These capsules are further encapsulated within an epoxy-amine polymeric shell. Similarly, the amine within the tiny capsules is released into the core of the larger capsule ultimately delivering the amine upon rupturing of the polymeric shells.

Use of interfacial condensation to encapsulate substances such as pharmaceuticals, pesticides and herbicides is taught in U.S. Pat. No. 3,577,515. The encapsulation process involves two immiscible liquid phases (typically water and an organic solvent), one being dispersed in the other by agitation, and the subsequent polymerization of monomers from each phase at the interface between the bulk (continuous) phase, and the dispersed droplets. Polyurethanes and polyureas are materials suitable for producing the microcapsules. The microcapsules comprising a polymeric sphere and a liquid centre, ranging from 30 micron to 2 mm in diameter, depending on monomers and solvents used.

Highly viscous and thickened hydrogels have been used to deliver pheromones, fragrances and other non-water soluble actives. U.S. Pat. No. 4,755,377, for example, describes a process of encapsulating perfume or fragrant material within an aqueous-based gel composition. The resulting material is in the form of a highly viscous semi-solid. U.S. Pat. No. 5,645,844 describes the use of chitosan paste for delivery of pheromones to disrupt insect mating, where the material can be dispensed by an apparatus such as a caulking gun. Due to their thickness and high viscosity, these materials, however, are generally unsprayable compositions.

Most hydrogels are safe and non-toxic to humans. Hydrogels have been used for the encapsulation of biological materials whereby the formulation is non-lethal to the viability of the cells, proteins, and related materials. U.S. Pat. No. 4,689,293, describes the process of encapsulating living tissue or cells. The encapsulation shell permits the passage of materials and oxygen to the cells and permits the diffusion of the metabolic by-products from the gel.

SUMMARY OF THE INVENTION

To provide an extended release period of an active, microbeads comprising a hydrophilic matrix with active-filled microcapsules entrained therein is provided. The hydrophilic matrix is capable of immobilizing a broad spectrum of microencapsulated active materials, either water soluble or non-water soluble. The microbeads may be suspended in a sprayable solution.

In an aspect of the invention, the hydrophilic matrix may be made from a water soluble matrix-forming material to provide an environmentally friendly microbead.

In a further aspect of the invention, the microbeads may be capable of rehydrating after an initial dehydration and release of active. Thus, the release and longevity of the active can be controlled by adjusting the humidity of the environment in which the microbeads have been delivered.

BRIEF DESCRIPTION OF THE DRAWINGS

FIG. 1 is a digital image of a light micrograph of a preferred embodiment (Example 3) of the invention, taken at 40× magnification.

FIG. 2 is a digital image of a light micrograph of another preferred embodiment of the invention (EXAMPLE 5), prior to dehydration, taken at 40× magnification.

FIG. 3 is a digital image of a light micrograph of the same sample of FIG. 2, after dehydration, taken at 40× magnification.

DETAILED DESCRIPTION OF THE PREFERRED EMBODIMENTS

It would be advantageous to provide a delivery system that can minimize shell rupturing of active-filled microcapsules, to delay and/or prolong the release of active materials. In view of the increasing awareness of insecticide toxicity to humans and other environmental concerns, it would be advantageous to provide an active delivery system having an extended release life and having a hydrogel material in order that it be non-toxic and bio-degradeable. It would also be advantageous to provide a system for sprayable, long-lasting active material delivery that would be applicable to a broad spectrum of actives thereby eliminating the issue of reactivity of the active with one of the membrane components.

The present invention involves immobilizing encapsulated active(s) material within a hydrogel matrix, where the immobilization is provided in a protective microbead format. The microbeads can be suspended in a solution to provide a deliver system for active materials, where the system is capable of providing extended release periods. The matrix provides physical protection to the microcapsules from external pressures such as those that can occur during a spray delivery, for example. This in turn, minimizes pre-mature capsule bursts (rupturing) and prolongs the release period of the active(s). Upon dehydration of the water from the hydrophilic matrix, the microcapsule containing the active material remains immobilized within the residual matrix. The active is able to then release into the desired environement by diffusion through the capsule shell or membrane, followed by diffusion past or through the hydrophilic matrix.

The microbeads of the invention comprise a matrix forming material, and is preferably substantially spherical. The matrix forming materials of the present invention are hydrophilic and water soluble. Entrained or finely dispersed within the matrix are microcapsules containing active material. Active materials that can be encapsulated and and then immobilized within the hydrogel microbeads include aldehydes, esters, alcohols, epoxy compounds, ethers, ketones, or combinations thereof. This invention is particularly advantageous for delivery of reactive ketones in which the double bond of the carbonyl group is conjugated with one or more double bonds, for example acetophenone where the carbonyl group is conjugated with double bonds of the aromatic ring.

Conventional active delivery systems (such as for delivery of pheromone) generally involve polyurea or polymethyleneurea encapsulation, where interfacial polymerization or in situ polycondensation occurs to provide microencapsulated products, respectively. These systems however, are typically limited to encapsulation of water non-soluble and/or non-alcohol active materials, due to, for example, the reactivity of alcohol with the isocyanate contained in the polyurea membrane. The present invention provides microbeads having matrix cores that can provide sufficient immobilization of oil soluble actives and alcohol actives such that the active can be delivered and sprayed by conventional techniques. The hydrophilic matrix preferably and advantageously imparts the capability of the hydrogel microbeads to immobilize oil-soluble and alcohol active materials and minimizes the risk of undesired reactivity between the active and its immobilizer. Thus, immobilization of active materials by use of the microbeads of the invention does not render the immobilized material inert or ineffective.

A further benefit from immobilizing active ingredients in hydrogel microbeads is the ability of the hydrogel to "swell" under humid conditions and shrink under dry conditions. As used herein, "swell" is descriptive of the behavior of a microbead, wherein the size (volume) is enlarged (increased) due to absorption of water. This is likely due to the hydrophilic nature of the matrix forming materials used to immobilize the active material.

In the presence of humidity, the hydrogel microbeads are preferably capable of absorbing moisture, rehydrating, and consequently releasing active material contained within the matrix. This behavior can be cyclical. Thus, by controlling the humidity (or dryness) of the ambient air, the release rate of active material from the microbeads can be controlled such that specific periods of release can be generally predicted. It is therefore possible with the present invention to release the active material on demand from the microbead. Release on demand, or "smart release," can be advantageous in those instances where release is preferred at certain times. The microbeads' ability to further release active from the matrix and may increase the longeveity of releasing effective amounts of active material. Preferably, the microbeads are delivered to an intended environment in effective amounts to obtain the desired effect. For example, microbeads having pheromones entrained therein, are preferably delivered to a desired area in amounts such that mating disruption is effected and release is accomplished for more than 4 weeks, more preferably, the microbead can release for more than about 6 weeks; and most preferably more than about 8 weeks.

During the drying process (i.e dehydration) a surface film layer will form as a result of water evaporation from the hydrophilic matrix. Both initially and during use, the microbeads are characterized by a large surface area to volume ratio, which helps maintain the rate of diffusion of the active material during use. Thus, it has been found that microbeads made according to the method of present invention provide excellent delivery systems as they are capable of releasing active material for extended periods. Furthermore, since the active is dispersed within a water-based matrix, additional protection from environmental conditions (i.e., UV) can be provided.

Although it has been found that microbeads of the invention can be made having a diameter of up to about 5 millimeters (mm), it is preferred that the microbeads be between about 1 micrometers ($\mu$m) to about 1000 $\mu$m and more preferably between about 1 $\mu$m to about 500 $\mu$m in diameter to ensure that the microbeads are easily sprayable from conventional spray nozzles. Most preferably, to ensure minimal clogging in conventional nozzles, the microbeads are less than about 400 $\mu$m in diameter. It is conceivable, however, that with the advent of larger spray nozzles not currently used in the industry, the microbeads can be provided in much greater diameters.

For, spraying applications, particularly aerial spraying, it is desirable that the microbeads be capable of remaining suspended in solution (water) to ensure that the microbeads do not sink, settle, or coagulate in the suspension. This also ensures an even spray coverage. Preferably, the microbeads of the invention are able to remain in suspension, thus minimizing if not eliminating the need to agitate during application and optionally, during storage. Various suspension aids can also be included in the suspension containing the microbeads of the invention. Examples of suitable suspension aids include rhamsam gum, xanthum gum, gellan gum, pectin, and gum arabic.

Owing to the handling to which the microbeads are subjected, it is desirable that the microbeads of the present invention should be somewhat elastic, and not frangible. For example, atomization of a suspension during a spray application may force the suspension through two rotating perforated discs that are immediately upstream of the discharge nozzle. Sufficient elasticity of the microbeads minimizes physical damage to the microbeads as they pass through the discs.

Figure 1:
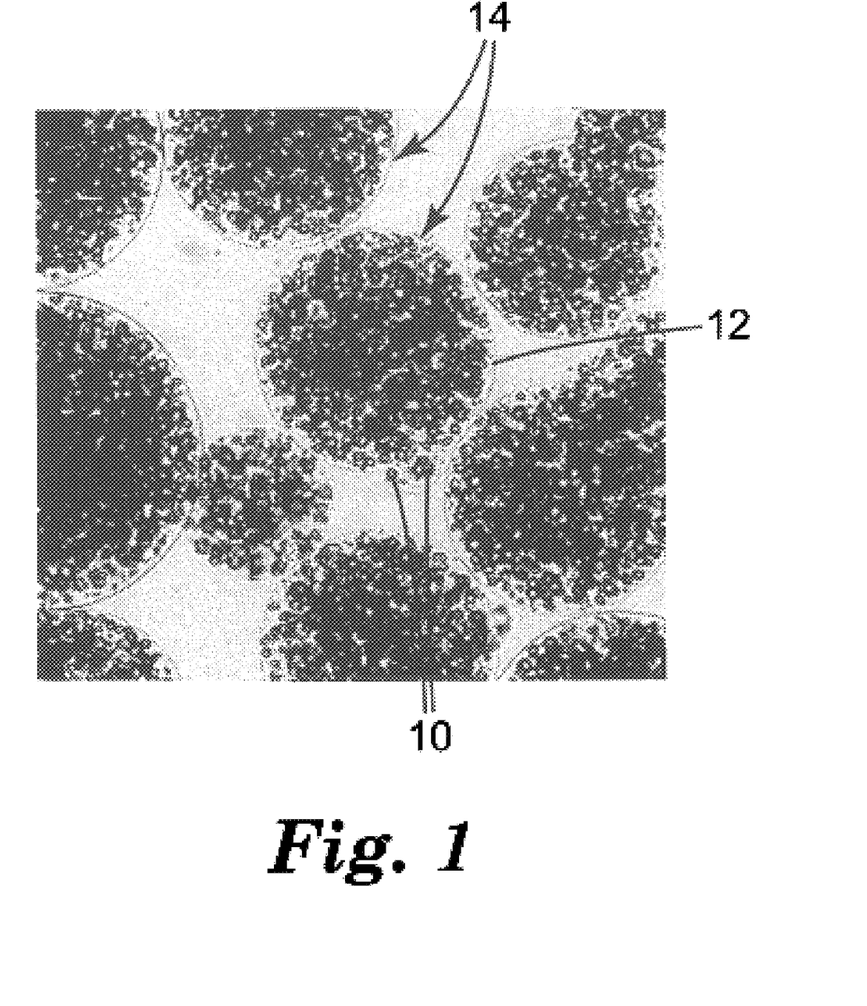

The microbeads of the present invention comprise a matrix forming material and active material. Referring now to FIG. 1, microbeads 14 of a preferred embodiment is shown, where a plurality of active-filled microcapsules 10 are entrained within hydrophlic matrix 12. As seen in FIG. 1, microcapsules 10 containing active material are preferably located between and within hydrophilic matrix 12, where matrix 12 provides an immobilizing network around the droplets. The degree and extent of agitation as well as the type of surfactant used to form the microbeads can affect the size and the dispersity of microcapsules within microbead's matrix. Entrained microcapsules 10 are preferably between about 0.01 nm to about 300,000 nm in diameter. More preferably, the microcapsules are between about 0.5 nm to about 200,000 nm in diameter.

The matrix-forming material useful in the present invention are biocompatible, water-soluble, have pendant functional groups, and complex with ions (e.g., polyvalent cations and/or anions) to form hydrogels. Functional groups of the matrix forming material include for example, carboxyls, hydroxyls, primary or secondary amines, aldehydes, ketones, esters, and combinations thereof. Preferably the hydrophilic matrix-forming material can be made from naturally occuring polysaccharides, such as alginates, chitosans, gums, agars, carrageenans, or the matrix can be made synthetic, water soluble monomers, oligomers or polymers, such as, for example, polyvinyl alcohol, poly(N-isoproylacrylamide), acrylamides, acrylates, and methacrylates, or combinations thereof.

Suitable naturally occurring polysaccharides include the water-soluble salts of alginic, pectic and hyaluronic acids, the water-soluble salts or esters of polyglucuronic acid, polymanuronic acid, polylygalacturonic acid and polyarabinic acid, and gum kappa-carrageenan. The preferred polysaccharides are the ammonium, magnesium, potassium, sodium and other alkali metal salts of alginic acid, and the most preferred polysaccharide is sodium alginate.

"Alginate" is the general name given to alginic acid and its salts. Alginates are composed of D-mannosyluronic (mannuronic—"M") and L-gulopyranosyluronic (guluronic—"G") acid residues. The alginate used to immoblize active droplets should be carefully selected to ensure proper microbead formation, ensure the stability of the microbeads during storage and delivery applications, and ensure that the microbeads are able to shrink and swell appropriately to deliver the desired active material over an extended period of time (preferably 4–6 weeks). Preferably, an alginate is chosen such that the matrix formed is sufficient in strength to withstand the shear forces (conditions) placed upon the microbeads during application via a spray nozzle—i.e., the microbeads are resistant to rupture during the spray application.

For strength and stability of the microbeads, it is desirable to choose the molecular weight and M:G ratio of the alginate to obtain preferred properties of the ultimate matrix. Although alginates high in mannuronic acid are generally useful for thickening applications, whereas alginates with a high level of guluronic acid are often used for forming gels, both alginate categories (individually or a mixture thereof) are suitable for the microbeads of the invention. A preferred alginate that imparts strength and rupture resistance is an alginate that has a high level of guluronic acid, e.g., greater than about 30 percent by weight. Alginate compositions with excessive levels of mannuronic acid could result in less stable and less rigid microbeads than high guluronic acid gels. However, high mannuronic acid alginates impart to the microbeads the capability of swelling and absorbing more water than microbeads of high guluronic acid content. Thus, a careful balance of the advantages imparted by each of M and G residues should be considered when choosing a suitable alginate.

Preferably, alginates used in the microbeads of the invention have a molecular weight in the range of about 100,000 kg/mol to about 2,500,000 kg/mol, more preferably about 200,000 kg/mol to about 1,500,000 kg/mol. Furthermore, the alginates preferably have an M:G ratio in the range of about 0.2 to about 3.5; more preferably about 0.3 to about 1.85.

Preferred alginates have a high level of guluronic acid, for example are alginates from the algae *Laminaria hyperborea*, stem, whole plant or frond. Preferred alginates with high levels of mannuronic acid include *Ascophyllum nodosum*, for example.

Gel matrices formed by crosslinking polysaccharides bearing pendant carboxylate groups are also useful in the present invention. These compounds are composed of water-insoluble alginates which include, with the exception of magnesium and the alkali metal salts, the group II metal salts of alginic acid. The water-insoluble alginate gels are typically formed by the chemical conversion of water-soluble alginates, in an aqueous solution, into water-insoluble alginates. This conversion usually is accomplished by the reaction of a water-soluble alginate with polyvalent cations released from a soluble di- or trivalent metal salt.

Water-soluble alginates can include the ammonium, magnesium, potassium, sodium, and other alkali metal salts of alginic acid. Water-insoluble di- or trivalent metal salts suitable for the present invention should satisfy two requirements: (1) that the water-insoluble metal salt contain a di-or trivalent metal ion capable of complexing with the pendant carboxylate groups of the water-soluble polysaccharide to cause the formation of a water-insoluble polysaccharide gel; and (2) that the water-insoluble metal salt reacts with a water-soluble acid to form a water-soluble metal salt.

A common and suitable alginate gel is composed of calcium aliginate.

Sources for the crosslinking calcium ions used in the formation of alginate gels include, for example, calcium carbonate, calcium sulfate, calcium chloride, calcium phosphate, calcium tartrate, calcium nitrate, and calcium hydroxide. Other acceptable crosslinkers may include lanthanum chloride, ferric chloride, cobaltous chloride, as generally are other compounds with multivalent cations, such as calcium ($Ca^{++}$), copper ($Cu^{++}$), barium ($Ba^{++}$), strontium ($Sr^{++}$) and the like.

The time of gelation of the calcium alginate gels can be accomplished by regulating the concentration of free calcium ions in the solution. Typically the concentration of free calcium ions is controlled by manipulation of the ionization rate of the calcium salt and/or by the inclusion of other compounds in the solution which react with the free calcium ions.

Advantageously, it is possible to immobilize a wide range of active materials, including non-water soluble materials as well as alcohols.

Preferred active materials entrained as droplets or microcapsules within the matrix are partially water-miscible organic molecules of compounds that have a molecular weight in the range of between about 100 to about 400, preferably between about 150 to 300. The compounds contain a heteroatom that confers some degree of water-miscibility. For many compounds of interest the sole heteroatom is oxygen, and there may be up to three heteroatoms per molecule in, for instance, hydroxy-substituted or keto-substituted carboxylic acids. Unsubstituted carboxylic acids of course contain two oxygen atoms and simple aldehydes, ketones and ethers contain only one oxygen atom. Compounds that contain nitrogen and/or sulphur atoms are also of interest.

Of particular interest are biologically active compounds. For purposes of the present invention, the term "biologically active" means materials that affect the life processes of organisms. Materials that are biologically active include herbicides, pesticides, pharmaceuticals, and semiochemicals, including naturally and artificially produced pheromones and synthetic pheromone analogs. Materials of this nature that are of particular interest are those materials that interfere with a life process essential to the survival of a target pest.

The method of the invention can be used to immobilize pheromone with functional groups such as acetates, aldehydes, ketones, alcohols, esters, epoxies, ethers, or combinations thereof. Pheromones may be defined as compounds which, when naturally produced, are secreted by one member of an animal species which can influence the behaviour or development of another member of the same animal species. Pheromones are species-specific and therefore the application of pheromones for insect behaviour modification has minimal effect on non-target pests. Pheromones supplied for modification of insect behaviour interfere with the "mate finding process" by releasing point sources of pheromone, which may compete with or camouflage the pheromone plume of a female. This latter type of action differs from chemical insecticides or insect growth regulators or hormones, in that pheromones target future generations of insects, not present ones. As pheromones are very species-specific and are used only in small quantities, their use is more environmentally acceptable than broadcasting of pesticides.

Many pheromones have an ester terminal group, for example and acetate or formate group. Typically these substances are water-immiscible and incorporation of them into microcapsules by known methods presents no particular problem. Many other pheromones have an aldehyde or an alcohol terminal group. In general, these are partially water-miscible and potentially reactive with the reactants used to encapsulate by prior, conventional methods. In particular, it is difficult to achieve high degrees of encapsulation of materials that have some degree of water solubility, as the material partitions between the small amount of organic solvent and the relatively larger amount of water that constitutes the continuous phase. Furthermore, these compounds can be expected to react with the reactants used to encapsulate. Aldehydes and ketones react with amines to form aldimines and ketimines, respectively. Alcohols, carboxylic acids and mercaptans react with isocyanates. Epoxy compounds react both with amines and with isocyanates. Thus, the present invetion overcomes the limitation of delivering partially water-miscible substances such as alcohols, aldehydes, carboxylic acids, ketones, ethers, including epoxy compounds, and mercaptans.

Pheromones useful in the inventive microbeads are preferably insect pheromones. In describing the structure of the a pheromone, the following notation is used: the type (E(trans)or Z(cis)) and position of the double bond or bonds are given first, the number of carbon atoms in the chain is given next and the nature of the end group is given last. To illustrate, the pheromone Z-10 C19 aldehyde has the structure;

Pheromones can be mixtures of compounds with one component of the mixture predominating, or at least being a significant component. Partially water miscible significant or predominant components of insect pheromones, with the target species in brackets, include, for example: E/Z-11 C14 aldehyde (Eastern Spruce Budworm), Z-10 C19 aldehyde (Yellow Headed Spruce Sawfly), Z-11 C14 alcohol (Oblique Banded Leafroller), Z-8 C12 alcohol (Oriental Fruit moth) and E,E-8,10 C12 alcohol (Codling moth), E-11 C14 acetate (Sparganothis Fruitworm), and Z-11 C14 acetate (Blackheaded Fireworm).

An example of a ketone that is a pheromone is E or Z 7-tetradecen-2-one, which is effective with the oriental beetle. An ether that is not a pheromone but is of value is 4-allylanisole, which can be used to render pine trees unattractive to the Southern pine beetle.

Preferred embodiments of the invention are described with reference to immobilization of partially water-miscible and water immiscible pheromones, but it should be appreciated that the invention extends to immobilization of materials other than such pheromones and to microbeads containing materials other than pheromones. Those materials may, or may not, be biologically active.

For example, alternatively, active materials containing mercaptans can be immobilized in the microbeads of the invention, such as what is found in urine of animals. These compounds are preferable in situations where animals mark their territory by means of urine, to discourage other animals from entering the particular territory. Examples of such animals include preying animals such as wolves, lions, dogs, etc. By dispersing hydrogel microbeads containing the appropriate mercaptans, it is possible to define a territory and discourage particular animals from entering that territory. For example, the urine of a wolf includes a mercaptan, and distribution of microbeads from which this mercaptan is gradually released to define a territory will discourage deer from entering that territory. Other active materials useful in discouraging approach of animals include essences of garlic, putrescent eggs and capsaicin.

Other active compounds that can be included in the microbeads of the invention include perfumes, fragrances, flavouring agents and the like.

Optionally, oil absorbents can be incorporated into the active droplets. These absorbents can help retain the active droplets within the microbeads, resulting in longer lasting formulations. Clays and starches could alternatively be used for this purpose.

The concentration of active material in the microbeads of the invention should be at a level such that the matrix forming material can still provide a strong, rupture resistant network and deliver an effective amount of the active material to the environment to which it is intended. Thus, the active material is preferably present in an amount between about 0.1 wt % to about 60 weight percent (wt %) of the total weight of the microbead. More preferably, the amount of active material is present in the microbead at between about 0.2 wt % to about 40 wt %; and most preferably between about 0.3 wt % to about 20 wt %.

The microbeads of the present invention are preferably delivered in suspension in aqueous or solvent-based solutions. For environmental and biologically-friendly reasons, it is preferred that aqueous suspensions be used. Suspension aids are preferably included in the suspension formulations to ensure the microbeads remain suspended in solution.

Preferably, the suspension solution is substantially free of monovalent cations, such as sodium, to avoid degradation or breakdown of the microbeads. In a preferred aspect, a concentration of approximately 50 millimolar of a crosslinker such as calium chloride is maintained in a stored solution comprising the microbeads of the invention.

Optionally, adhesive material can be included in the compositions of the invention to assist in retention of the microbeads to an intended substrate. The adhesive material can be provided in various forms, such as for example, latex or a tacky microspheres. Adherent properties imparted to the hydrogel microbeads should result in the microbeads being able to still retain their suspended state and minimize aggregation or coagulation in the aqueous suspension. Furthermore, any adhesive material used to impart adherent properties should not affect the integrity of the particles; it should not dissolve or weaken the microbead(s).

A suitable adhesive material that may be included in the compositions of the invention is adhesive latex. The adhesive latex may be any suitable water-dispersible adhesive available in the art. In the agricultural business, such latex compositions are often called stickers or spreaders. Stickers are used to help non-encapsulated agriculture chemicals adhere to plants. Spreaders are used to help disperse non-encapsulated agriculture chemicals on application. Preferred adhesives are acrylate-based adhesives. One suitable latex is available from Rohm & Haas under the trade designation COMPANION. Another is available from Deerpoint Industries under the trade designation DPI S-100 (a proprietary sticker/spreader). Examples of such adhesives are polymers made from the "soft" monomers such as n-butyl acrylate, isooctyl acrylate, or the like, or copolymers made from a soft component, such as isobutylene, n-butyl acrylate, isooctyl acrylate, ethyl hexyl acrylate, or the like; and a polar monomer such as acrylic acid, acrylonitrile, acrylamide, methacrylic acid, methyl methacrylate or the like. Non-spherical polyacrylate adhesives are commercially available, for example, as the Rohm and Haas RHOPLEX line of adhesives. Preferably, the non-spherical polyacrylate adhesive is present in an amount of about 10–35% by weight of the total suspension.

Tacky microspheres of adhesive may alternatively be used to help adhere the hydrogel microbeads of the invention to an intended substrate. The tacky microspheres have sufficient adhesive properties to provide the desired adhesive function, yet there is no danger of completely coating the microbead which may lead to potentially inhibiting the release characteristics of the microbead. The combination of microbeads and tacky microspheres may be applied without the need to modify the orifices of conventional sprayers with minimal clogging or plugging problems. Furthermore, the incorporation of tacky (adhesive) microspheres to the (formulation) suspension of microbeads allows the microbeads' surfaces to become tacky. The beads can therefore stick to intended surfaces, such as, foliage and branches, for example. The adhesive microspheres, especially if they are hollow, may also absorb some of the active material into its own body, thus providing a second mechanism of release of the active material. This could result in an overall alteration, preferably an enhancement, of the release profile.

Preferably, the adhesive material is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569. Other suitable adhesives are the tacky microspheres having pendant hydrophilic polymeric or oligomeric moieties that are disclosed in U.S. Pat. No. 5,508,313.

Alternatively, the adhesive comprises between about 60–100% by weight of hollow, polymeric, acrylate, inherently tacky, infusible, solvent-insoluble, solvent dispersible, elastomeric pressure-sensitive adhesive microspheres having a diameter of at least 1 micrometer, and between about 0–40% by weight of a nonspherical polyacrylate adhesive. The hollow microspheres are made in accordance with the teaching of European Patent Application 371,635.

The compositions of the present invention may also include one or more adjuvants including, for example, gelling aids, preservatives, dyes, humectants, fixatives, emulsifiers, extenders, and freeze/thaw stabilizers such as polyhydric alcohols and their esters. These materials are present in an amount effective to achieve their extended function, generally less than about 5% typically less than 2%, by weight of the composition.

Incorporation of a light stabilizer can be included in the microbeads of the invention. Suitable light stabilizers include the tertiary phenylene diamine compounds disclosed in Canadian Patent No. 1,179,682, the disclosure of which is incorporated by reference. The light stabilizer can be incorporated by dissolving it, with the active, in a water-immiscible solvent. Alternatively, a light stabilizer can be incorporated in the microbeads as taught in Canadian Patent No. 1,044,134, the disclosure of which is also incorporated by reference.

Microencapsulated active materials are preferably formed using conventional polyurea and/or polymethyleneurea encapsulation techniques such as what is taught in in U.S. Pat. Nos. 3,691,140; 5,045,569; and 5,508313 as well as European Patent Application 371,365, all of whose teachings are incorporated here by reference. Alternatively, microcapsules having gelatin shells may be used in the microbeads of the invention and prepared by the methods provided in U.S. Pat. No. 4,402,856. In another preferred embodiment, microcapsules may alternatively be provided in the form of a liposome, and prepared by the processes taught in U.S. Pat. No. 4,911,928.

The process of making the microbeads of the invention, preferably comprises, making the active filled microcapsules and dispersing the microcapsule suspension in the hydrophilic matrix-forming material. The mixture is then hardened (gelled) to form microbeads. The resulting microbead is a hydrogel microbead, having greater than about 30% water initially, and the active-filled microcapsules would be dispersed and entrained within the water-polymer matrix.

The hydrophilic matrix with the microcapsules entrained in the matrix can be formed either by ionic interactions or by thermal setting. When forming microbeads by ionic interactions, there are two preferred methods of forming: (1) the spray method and (2) the emusification method. In the spray method, the matrix-forming/active suspension mixture is mixed and then atomized mechanically to form small spherical droplets. The size of the microbeads is generally governed by the intrinsic properties of the emulsion suspension, the feed rate and the coaxial airflow rate.

The droplets which are atomized can then be allowed to free-fall directly into a reacting bath. The reacting bath cures or sets the hydrogels so that they solidify. Reaction bath curing can be achieved through chemical or non-chemical means. For the case of sodium alginates, calcium ions are used to cross-link the polymer chains. A preferred crosslinker is calcium chloride.

Alternatively, an emulsification method can be used to produce hydrogel microbeads. In selecting the continuous phase material, it is preferable that it be immiscible with the aqueous matrix forming material.

The matrix-forming material preferably has a range of concentrations usable in practicing the invention. The concentration should be chosen to optimize ease of handling, gelling time, the strength of the hydrogel microbead around the active material droplets. For example, a sodium alginate solution can preferably be prepared in a concentration of about 1 to about 10% (w/v) in water, more preferably about 1.5 to about 5% and most preferably from about 1 to 3%. However, if the hydrogel agent concentration is too great, the solution may be so viscous as to hinder the formation of spherical microbeads.

Alternatively, hydrogel microbeads of the invention can be formed, for example, by adding the matrix forming material solution drop-wise to a selected crosslinker. For example, a method can be used whereby droplet formation and crosslinker addition is completed as a one step process by a vibrating nozzle which ejects a hydrogel droplet from one source and coats the droplet with a crosslinker from another. U.S. Pat. No. 4,701,326 teaches use of this method.

In the preferred aspect where alginates are used to immobilize an active material, a crosslinker is preferably made up in solution at a concentration of 1 to 1000 millimolar, more preferably 20 to 500 millimolar and most preferably from 50 to 100 millimolar. The concentration ranges may have to be adjusted, depending on the nature of a crosslinker and matrix-forming material.

The microbeads containing matrix material and active material can be treated with the crosslinker solution by soaking, spraying, dipping, pouring or any of sever other methods which will deposit an amount of the complexing agent on the droplet. When soaking, the time in solution may be from 1 second to 24 hours, preferably 1 minute to 1 hour, and more preferably from 10 to 30 minutes.

The temperature for hydrogel microbead formation is preferably chosen as to avoid damage or alteration to the active material. For example, in the preferred aspect where alginates are utilized, the temperature is preferably in the range of about 1° C. to about 70° C.; more preferably between about 10° C. to about 40° C., and most preferably between about 15° C. to about 30° C.

To immobilize active-filled microcapsules within a temperature setting matrix, the matrix-forming material must first be solubilized in water using heat. The heating temperature is preferably be within a range of about 40° C. to about 100° C. When the matrix-forming material is completely dissolved, the temperature of the solution is lowered such that the solution is about 5° C. to about 10° C. above the gel setting temperature. A suspension containing active-filled microcapsules is then preheated to a similar temperature to that of the matrix-forming solution, afterwhich the two mixtures are blended together and mixed homogeneously.

To produce the microbeads, the molten matrix-forming/microcapsule suspension can be atomized through a nozzle system or be emulsified using an oil type continuous phase. In the spray method, the molten suspension can be atomized using coaxial air, for an example, and dropped into an ice bath containing distilled water. The matrix is then formed, entraining the microcapsules therein.

To produce the microbeads using the emulsification method, a continuous oil phase is preheated in a jacketed reactor to the temperature of the molten microcapsule suspension. The continuous phase may be any hydrophobic liquid. The preferred and most convenient liquid is a vegetable oil or mineral oil. Other possible hydrophobic liquids may include hydrofluorethers, siloxanes, or solvents such as cycloxhexanes and chloroforms. The microcapsule suspension is then emulsified in the continuous phase with the aid of a mixer. The mixing is continued until a desired particle size is obtained. The temperature of the reaction mixture is then lowered to that of ice water (about 5° C.). The matrix is then formed, entraining the microcapsules therein. The microbeads can then be filtered and washed prior to suspending them in solution for delivery.

Surfactants may be used in the process of forming the microbeads. The incorporation of different surfactants will offer different types of microemulsion drop sizes of the active within the hydrogel as well as dictate the amount of free oil lost in the reacting bath solution. A preferred surfactant has a high critical micelle concentration, such as for example, a product available under the product designation DISPONIL SUS IC 875 (CMC~1%), available from Henkel (Ambler, Pa.).

Particularly preferred surfactants are nonionic. Examples of suitable surfactants include polyvinylpyrrolidone (PVP) and poly(ethoxy)nonylphenol. PVP is usable and available at various molecular weights in the range of from about 20,000 to about 90,000. PVP having a molecular weight of about 40,000 is preferred. Poly(ethoxy)nonylphenols are commercially available under the trade designation IGEPAL from Rhone-Poulenc (Cranbury, N.J.), with various molecular weights depending on the length of the ethoxy chain. Poly(ethoxy)nonylphenols having the formula:

where n has an average value from about 9 to about 13 can be used. A preferred poly(ethoxy)nonylphenols is available commercially under the product name IGEPAL 630, from Rhone-Poulenc (Cranbury, N.J.)—630 is indicative of the approximate molecular weight of the compound. Other examples of suitable surfactants include polyether block copolymers, such as those available under the trade designations PLURONIC and TETRONIC, both available from BASF (Washington, N.J.), polyoxyethylene adducts of fatty alcohols, such as BRIJ surfactants available from ICI (Wilmington, Del.), and esters of fatty acids, such as stearates, oleates, and the like. Examples of such fatty acids include sorbitan monostearate, sorbitan monooleate, sorbitan sesquioleate, and the like. Examples of the alcohol portions of the fatty esters include glycerol, glucosyl and the like. Fatty esters are commercially available as surfactants under the trade designation ARLACEL C from ICI (Wilmington, Del.)

Various properties of the surfactant, such as for example, chain length, functional groups, and hydrophobic regions, can affect the size of the active droplets formed within the microbeads. For example, use of PVP (having a molecular weight of 40,000) tend to result in production of larger sized active droplets than use of poly(ethoxy)nonylphenols (IGEPAL 630).

Ionic surfactants can alternatively be used in the processes of the invention. Examples of suitable ionic surfactants partially neutralized salts of polyacrylic acids such as sodium or potassium polyacrylate or sodium or potassium polymethacrylate.

The microencapsulated active material entrained in the microbeads of the invention are released gradually over time. This is a variant of the meachanism that could occur with conventional microencapsulated materials that do not have a hydrophilic matrix to cushion and protect the active, since an unprotected microcapule could potentially release the active ingredient nearly all at one time, for example at the time of shell rupture. Active release from the microbeads of the invention is preferably and advantageously controllable by controlling the humidity (and dryness) of the environment in which the microbeads are located.

While not being bound by this theory, it is believed that one mechanism of release of the active involves water evaporation from the gel matrix followed by the diffusion of active through the microcapsule shell or membrane and then through the hydrophilic matrix. Release (diffusion) by this mechanism could result in a delayed release of the active. In another theorized mechanism, the active becomes entrained in the water from the matrix, and as the water evaporates, the active releases into the atmosphere.

In preferred applications, these hydrogel microbeads would be sprayed followed by water evaporation within the gel. As the hydrogel bead dehydrates, the matrix shrinks in size and releases its active with time. The degree of shrinkage of the microbead from its original size, depending on the components used in the formulation. Preferably, the microbeads shrink about 10% to about 90% from its original size, more preferably from about 40% to about 80%, and most preferably from about 50% to about 70%.

Advantageously, the microbead, upon re-exposure to humidity, can swell and rehydrate itself by absorbing water. Re-exposure to humidity can be performed in various ways. For example the microbeads' surfaces can be contacted directly with water or other aqueous solutions. In agricultural applications where pheronomes are used as the active material, a farmer or caretake can irrigate the plants and foliage to re-hydrate the hydrogel microbeads. Alternatively, the humidity of the environment or ambient air in which the microbeads are located in can be increased by entraining air droplets in the air. Thus, the microbeads can be "re-activated" by re-hydration, thereby selectively controlling the release times of the active material.

The microbeads of the invention can be delivered to an intended substrated by various methods. In the preferred embodiment where the active material is a pheromone, delivery of the microbeads will depend on various factors, such as for example, the size of release coverage desired. For small concentrated areas, the microbeads can be impregnated into hollow fibres, plastic laminate flakes or twist-ties and then physically attaching the fibres or ties to plants to be protected from insect infestation. For larger areas, spraying (aerially or by back-pack) may be the better option.

All patents cited in this specficiation are hereby incorporated by reference.

The following examples are for illustration purposes only and are not meant to limit the scope of the invention. Unless otherwise specified, all parts and percentages are by weight.

EXAMPLES

Preparatory Examples

The microencapsulation procedures disclosured in U.S. Pat. Nos. 3,691,140; 5,045,569; and 5,508,313 and European Patent Application 371,365 were followed to prepare microencapsulated active materials. An aqueous suspension of microcapsules of each of the pheromones in Preparatory Samples A through C were encapsulated in a polyurea shell (50 g) and Rhamsan gum suspended suspending agent were added, with stirring. Discrete spherical microcapsules were produced with a size range of 10 to 100 microns and a mean diameter of about 50 microns.

Preparatory Sample A: Z7-Z11-C16 acetate and Z7-E11-C16 acetate (1:1)

Preparatory Sample B: E11-C14 acetate

Preparatory Sample C: E11-C14 alcohol

It was noted that the microcapsule shell wall of Sample C was not as strong compared to microcapsules formed by Sample A & B. Microcapsule walls of Sample C broke down once the water was evaporated away leaving a pool of pheromone.

Example 1

Microbeads Formed by Spray Method

A sodium alginate solution was initially prepared by dissolving a preweighed amount of alginate into a known volume of distilled water. The solution was mixed thoroughly to solubilize the polymer and was deaerated for removal of entrained air bubbles. In a separate 250 mL vessel, 80 g of a 2% alginate solution (SKW; Lannilis, France) was mixed with 20 g of polyurea microcapsule suspension (Preparatory Sample B) at a speed of about 300 RPM using a marine type impeller (3 cm diameter). The microcapsule suspension was then atomized into fine particle droplets using a coaxial air nozzle sprayer into a calcium chloride bath (50 mM concentration). The size of the particles was determined by the settings on the atomizing device. This involved control of the nozzle head diameters, the feed rate of the emulsion through the nozzle and the airflow which passed along its feed path. At a nozzle feed diameter was 0.508 mm, the coaxial air nozzle was 1.17 mm in diameter, the feed pressure was about 140 kPa, and the airflow was about 35 kPa fine particles were formed. Discrete spherical microbeads having polyurea microcapsules entrained in the alginate matrix were obtained, the microbeads having a mean diameter of about 500 microns.

Example 2

Microbeads Containing Alcohol Type Pheromone Microcapsules

The procedure outline in EXAMPLE 1 was adopted and followed except that the microcapsules used were polyurea containing E11-C14 alcohol (Shin-Etsu Chemical Co., Ltd.; Tokyo, Japan) obtained from Preparatory Sample C. The resulting microbeads were discrete and immobilized the microcapsules without damaging the polyurea shell. Upon dehydration of the hydrogel, the alginate matrix appeared to envelope the polyurea microcapsule such that the particles remained intact.

Example 3

Microbeads Using an Emulsification Method

An agarose solution (Aldrich Chemical Co.; Milwaukee, Wis.) was initially prepared by dissolving a preweighed amount of agarose into a known volume of distilled water. The solution was mixed thoroughly to solubilize the matrix forming solution by heating it to a temperature of about 100° C. The temperature of the matrix forming forming solution was then lowered until it approached the setting temperature (usually between 40–70° C. depending on the polymer used). Equal weights of a polyurea microcapsule suspension containing pheromone (Preparatory Sample A) was preheated to about 40–70° C. and mixed with the matrix forming solution while maintaing the temperature somewhere between 40–70° C. 50 g of this warm microcapsule suspension was poured into a 500 mL glass jacketed reactor set to a temperature of about 60° C. containing 200 g of light mineral oil (Drakeol 34; Penreco; Karns City, Pa.). The mixture was mixed at 600 RPM using a disc turbine agitator (5.08 cm diameter) for about 2 minutes. The emulsion was then quickly cooled in an ice bath for 10 minutes. The microbead diameter ranged in size from 0.1 to 1.5 mm. The resulting microbeads contained immobilized microcapsules within a temperature setting agarose gel matrix.

Example 4
Microbeads Using an Emulsification Method

A carrageenan solution (SKW; Carenton, France) was initially prepared by dissolving a preweighed amount of K-carrageenan into a known volume of distilled water. The solution was mixed thoroughly to solubilize the matrix forming material by heating the solution to a temperature of about 80° C. Equal weights of a polyurea microcapsule suspension containing pheromone (Prepraratory Sample A) was preheated to about 80° C. and mixed with the matrix forming solution while maintaing the temperature at 80° C. 50 g of this warm microcapsule suspension was poured into a 500 mL glass jacketed reactor set to a temperature of about 80° C. containing 200 g of light mineral oil (Drakeol). The mixture was mixed at 600 RPM using a disc turbine agitator (5.08 cm diameter) for about 24 minutes. The emulsion was then quickly cooled in an ice bath for 10 minutes. 200 g of a 3% potassium chloride solution was added to the suspension to further cross-link the microbeads. The microbead diameter ranged in size from 0.1 to 1.5 mm. The resulting microbeads contained entrapped microcapsules within a temperature setting carageenan gel.

Example 5

Figure 2:
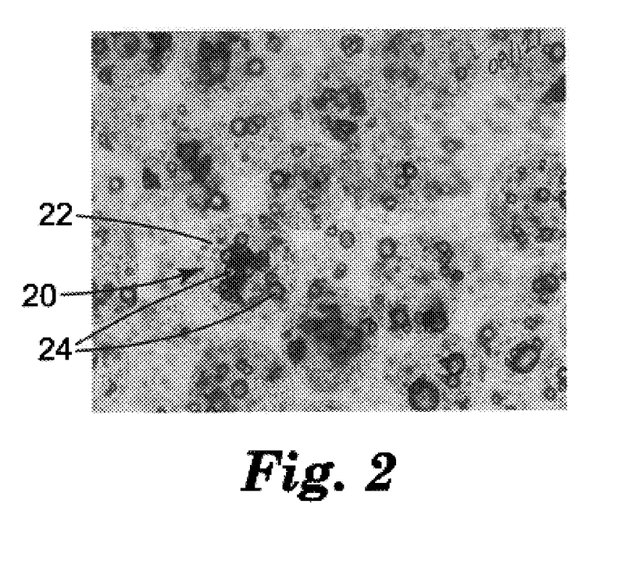
Figure 3:
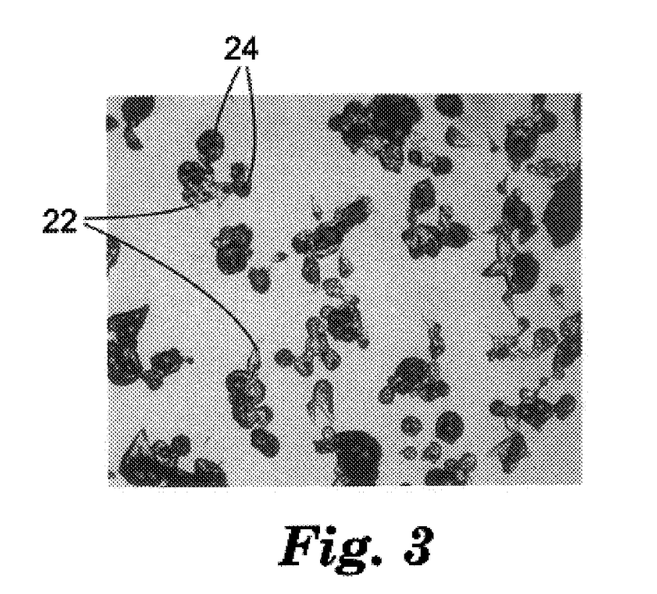

Microbeads were made using coaxial airflow atomization, using the formulation of Example 2. Average particle particle diameters were measured by evaluating 30–50 microbeads, using a light microscope, LEITZ DIAPLAN available from Ernst Leitz (Wetzlar, West Germany). The microbeads containing alcohol pheromone E11-C14 alcohol, obtained from Sample 2, were placed onto a microscope slide and microphotographed at a magnification of 40×. A digital image of the micrograph is provided in FIG. 2. As seen in FIG. 2, microbeads 20 comprise a matrix 22 having active-filled polyurea microcapsules 24 entrained in matrix 22. After exposing the microbeads to air at room temperature for about 8 hours, the same microbeads were microphotographed at the same magnification of 40×. Referring now to FIG. 3, a digital image of the micrograph taken after dehydration of the microbeads, it is shown that matrix 22 has shrunk and shrouded around microcapsules 24, where microcapsules 24 appear to be intact.

What is claimed is:

1. A method of delivering and releasing active material, comprising the steps of:
   (a) providing gelled beads, said beads being a hydrophilic matrix having microcapsules entrained therein, said microcapsules comprising a pheromone;
   (b) creating a suspension of a plurality of said beads;
   (c) delivering said suspension comprising said beads to an intended environment; and
   (d) allowing said beads to dehyhdrate.

2. The method according to claim 1 further comprising the steps of:
   (e) exposing said beads to humidity; and
   (f) allowing said beads to rehydrate.

3. The method according to claim 2 wherein said step of exposing said beads to humidity is performed by wetting the surfaces of said beads with a solution.

4. The method according to claim 2 wherein said step of exposing said beads to humidity is performed by adding moisture to the ambient air.

5. The method according to claim 2 wherein said steps c) thru e) are repeated sequentially.

6. The method according to claim 1 wherein said microcapsules are made from a material selected from the group consisting of polyurea, polymethylenurea, polyurethane gelatin, and lipisome.

7. The method according to claim 1 wherein said microbeads further comprise a plurality of active material droplets.

8. The method according to claim 1 wherein said hydrophilic matrix is selected from the group consisting of a polysaccharide, polyvinyl alcohol, polyacrylamides, and methacrylates.

9. The method according to claim 8 wherein said matrix is a polysaccharide selected from the group consisting of alginate, chitosan, carrageenan, gum and agar.

10. The method according to claim 1 wherein said active material is selected from the group consisting of a pheromone, mercaptan-containing compound, herbicide, pesticide, and pharmaceutical material.

11. The method according to claim 1 wherein said hydrophilic matrix is an alginate.

12. The method according to claim 1 wherein said bead has an average diameter between about 1 $\mu$m to about 1000 $\mu$m.

13. The method according to claim 1 wherein said bead has an average diameter between about 1 $\mu$m to about 500 $\mu$m.

14. The method according to claim 1 wherein said bead further comprises a surfactant.

15. The method according to claim 1 wherein said bead further comprises an oil absorbent.

16. The method according to claim 1 wherein said beads further comprise an additive selected from the group consisting of preservatives, humectants, stabilizers, UV protectants, and combinations thereof.

17. The method of claim 1 wherein said microcapsules are present in an amount between about 0.1 wt % to about 60 wt % of the total weight of said bead.

18. The method of claim 1 wherein said microcapsules are in an amount between about 0.2 wt % to about 40 wt % of the total weight of said bead.

19. The method of claim 1 wherein said microcapsules are present in an amount between about 0.3 wt % to about 20 wt % of the total weight of said bead.

20. The method of claim 1 wherein said microcapsules have a diameter of about 0.01 nm to about 300 $\mu$m.

21. The method of claim 1 wherein said microcapsules have a diameter of about 0.05 nm to about 200 $\mu$m.

22. A sprayable composition comprising beads suspended in a solution, wherein said beads comprise a hydrophilic matrix having a plurality of microcapsules containing pheromone entrained therein.

23. The composition of claim 22 wherein the beads further comprise active material droplets.

24. The composition of claim 22 further comprising adhesive material selected from the group consisting of hollow tacky adhesive microspheres, solid tacky adhesive microspheres, latex, and combinations thereof.

25. The composition of claim 22 wherein said beads further comprise a surfactant.

26. The composition of claim 22 wherein said beads further comprise an oil absorbent.

27. The composition of claim 22 wherein said beads further comprise an additive selected from the group consisting of preservatives, humectants, stabilizers, UV protectants, and combinations thereof.

* * * * *